United States Patent [19]

Phillips et al.

[11] Patent Number: 4,758,233

[45] Date of Patent: Jul. 19, 1988

[54] CREAM APPLICATOR

[75] Inventors: Ian R. Phillips, Killara; Robert H. Lodge, Deewhy; Glen W. Bunyan, Mona Vale, all of Australia

[73] Assignee: N.J. Phillips TPY. Limited, New South Wales, Australia

[21] Appl. No.: 39,623

[22] Filed: Apr. 16, 1987

[30] Foreign Application Priority Data

Apr. 22, 1986 [AU] Australia .............................. PH5572

[51] Int. Cl.⁴ .......................................... A61M 5/245
[52] U.S. Cl. ................................................. 604/232
[58] Field of Search ............... 604/232, 234, 235, 184, 604/187, 218, 224, 222; 222/46, 47

[56] References Cited

U.S. PATENT DOCUMENTS

| | | | |
|---|---|---|---|
| 3,023,751 | 3/1962 | Lipsky et al. | 604/235 |
| 3,848,593 | 11/1974 | Baldwin | 604/232 X |
| 4,020,838 | 5/1977 | Phillips et al. | 604/184 |

Primary Examiner—John D. Yasko
Attorney, Agent, or Firm—Ladas & Parry

[57] ABSTRACT

An applicator to inject a cream medicament into an animal, the applicator has a body which receives a cartridge consisting of a reservoir chamber and a delivery chamber, with a piston rod extending through both chambers. The applicator has trig operated means which causes reciprocation of the piston rod to cause delivery of the medicament.

8 Claims, 3 Drawing Sheets

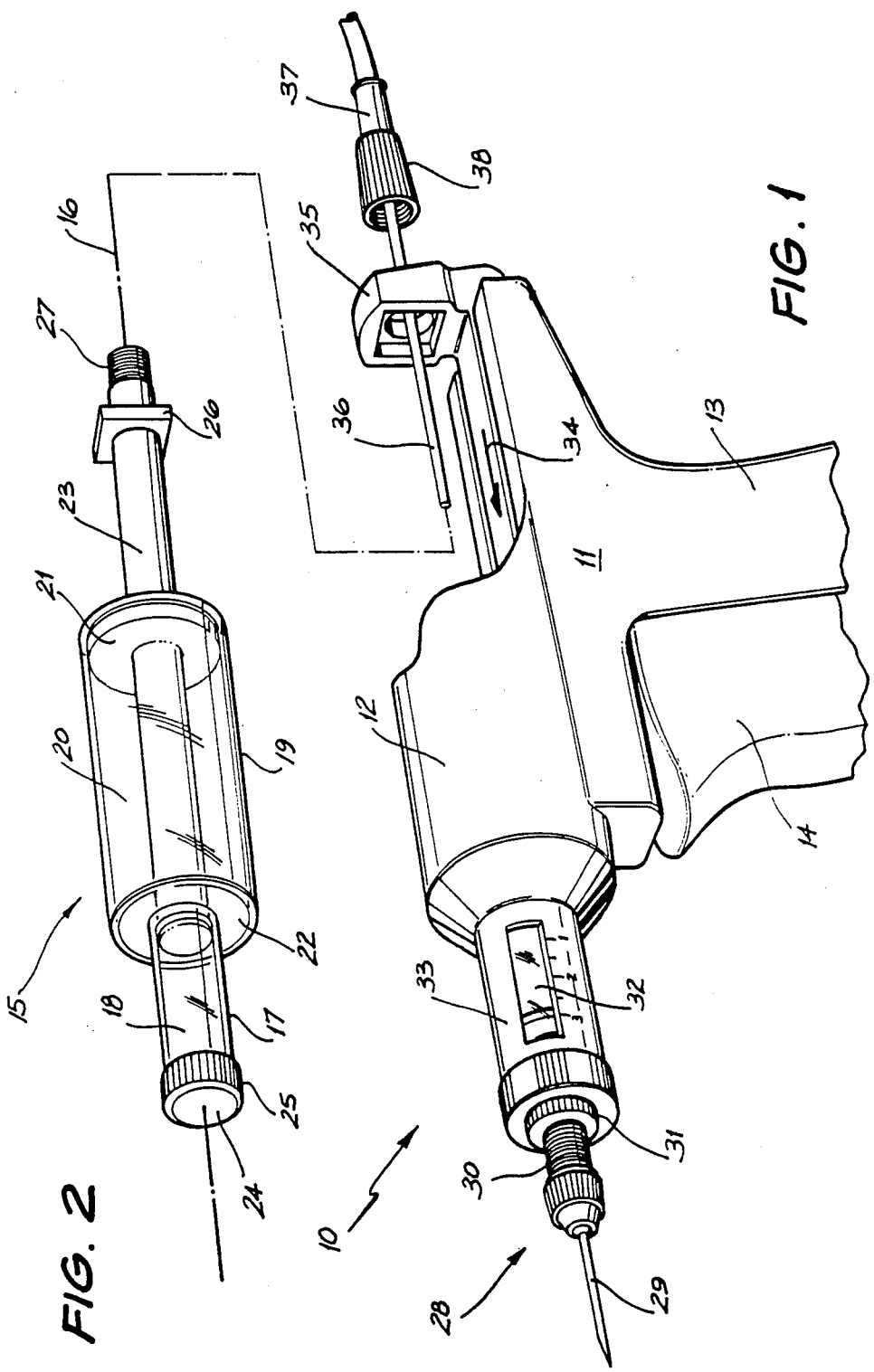

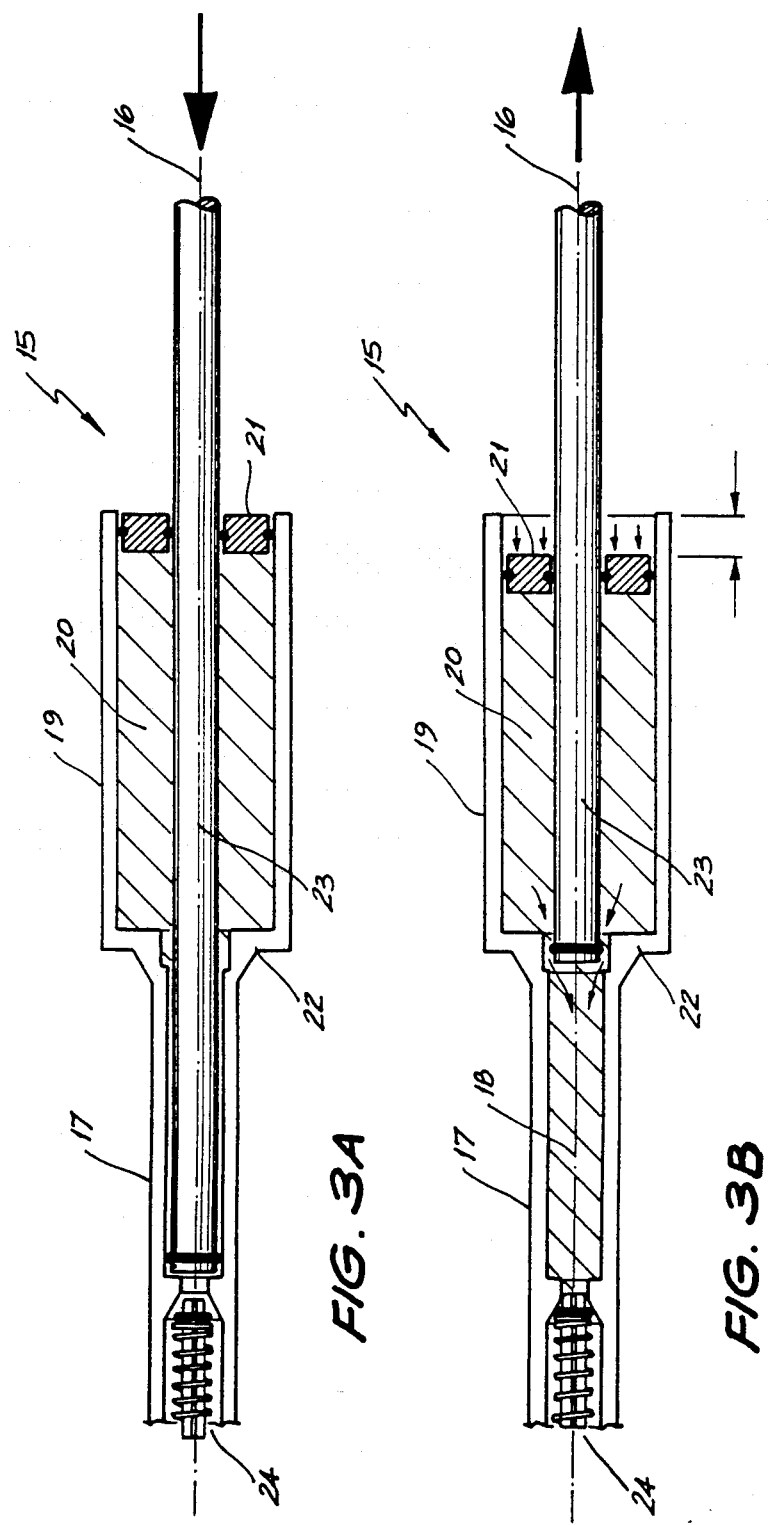

CREAM APPLICATOR

The present invention relates to injectors or applicators which deliver a medicament into an animal and more particularly but not exclusively to an applicator which injects a medicament, in the form of a paste or cream, into an animal.

Previously known applicators or injectors used to deliver a medicament into an animal have not used a disposal cartridge to contain the medicament. Accordingly, the entire device required cleaning for sterilisation purposes.

It is the object of the present invention to overcome or substantially ameliorate the above disadvantages.

There is disclosed herein a cartridge to receive a medicament to be dispensed, said cartridge having a longitudinal axis and comprising a delivery chamber, from which the medicament is dispensed, enclosed by a longitudinally extending side wall, a reservoir chamber enclosed by a further longitudinally extending side wall and having one end communicating with said delivery chamber and the other end closed by a sealed member movable longitudinally of said reservoir, a piston rod movable longitudinally through both chambers and sealingly engagable within said delivery chamber so that movement of said piston rod therealong delivers a predetermined volume of the medicament from within said delivery chamber, and the opposite movement of said piston rod exposes said delivery chamber to said reservoir chamber thereby enabling further medicament to be delivered from said reservoir chamber to said delivery chamber.

There is further disclosed herein an applicator to receive a cartridge of medicament and to dispense predetermined volumes of the medicament from the cartridge, the cartridge consisting of: a reservoir chamber and a delivery chamber, with a piston rod extending through both chambers and having one extremity sealingly received within the delivery chamber; said applicator comprising: a body having socket means to receive said cartridge; a piston rod actuator, having means to engage said piston rod, said actuator being movably supported on said body so as to be movable from a first position locating the extremity of said piston rod in said reservoir chamber, and a second position locating said extremity in said delivery chamber, so as to cause a predetermined volume of said medicament to be delivered from said delivery chamber; trigger means mounted on said body and adapted to be manipulated by a user; said trigger being operatively associated with said actuator means to cause reciprocation thereof between the first and second positions.

A preferred form of the present invention will now be described by way of example with reference to the accompanying drawings, wherein:

FIG. 1 is a schematic perspective view of an applicator to deliver a medicament into an animal;

FIG. 2 is a schematic perspective view of a cartridge to be employed in the applicator of FIG. 1;

FIGS. 3A and 3B are schematic sectioned side elevations of the cartridge of FIG. 2.

Figure 4:
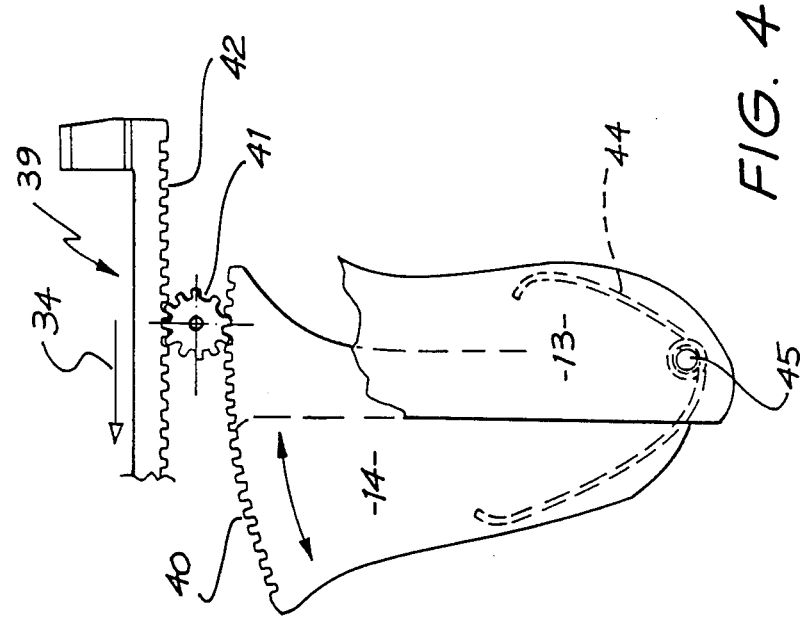
FIG. 4 is a schematic side elevation of the trigger mechanism of the applicator of FIG. 1.

In the accompanying drawings there is schematically depicted an applicator or injector 10 to deliver a medicament into an animal, and more particularly to inject the medicament into an animal. The applicator 10 includes a body 11 having a cartridge mounting 12, with a forward projection 33, to which there is fixed a handle 13. Pivotally mounted on the handle 14 is a trigger 14, by means of a pivot 44, which is manually manipulated by the operator. The mounting 12 is adapted to receive the disposable cartridge 15.

The cartridge 15 has a longitudinal axis 16 and consists of a first side wall portion 17 enclosing a medicament delivery chamber 18. A second side wall portion 19 is provided and which encloses a medicament reservoir chamber 20. The chamber 20 is closed at one end by means of a seal member 21 which is slidable longitudinal of the chamber 20 and sealingly engages the side wall portion 19. The other end of the chamber 20 is closed by means of a wall 22 to which the side wall portion 17 is attached. The chamber 18 is open at one end to the chamber 20. Extending through the chamber 20 and entering the chamber 18 is a piston rod 23 which slidably sealingly engages within the chamber 18 so that upon movement of the piston rod 23 towards the chamber 18, a predetermined dose of medicament is delivered from the end 24 of the cartridge 15. However, in the stored configuration, the end 24 is closed by a cap, or any other suitable seal 25. One end of the piston rod 23 has a threaded portion 27 and an abutment 26. The rear of the delivery chamber 18 is provided with an enlarged portion within which the end of the piston rod 23 is located when in the rest position.

The forward end of the body 11 is provided with a medicament delivery assembly 28 consisting of an injection needle 29 which communicates with the chamber 18 by means of a one-way valve assembly 43. The one-way valve assembly 43 restricts the medicament to move from the chamber 18 to the needle 29, but inhibits reverse flow. In this particular embodiment the valve assembly 43 is incorporated in the forward end of the cartridge 15, however the valve assembly could be mounted in the forward projection 33. The assembly 28 also includes an adjustment piston 30 which abuts the forward end of the cartridge 15 to restrict forward movement thereof to thereby determine the volume of medicament delivered. The adjustment piston 30 is threaded and engages a threaded member 31 which is rotated in order to position the piston 30 as required. The piston 30 positions the cartridges within the body 11 to vary the stroke of the rod extremity within. A side window 32 is provided to enable the position of the cartridge to be detected for volume adjustment purposes. Alternatively the forward end of the 24 of the cartridge could be threaded and extend through the projection 33. The threaded end 24 could then be engaged by the member 31 and movement of the whole cartridge 15 effected by rotation of the member 31.

The forward end of the body 11 includes a cylindrical wall 33 within which the side wall portion 17 is received.

Slidably mounted in the body 11 is a slide 39 which is caused to move in the direction of the arrow 34 upon direction of the trigger 14. One end of the slide 39 is provided with a yoke 35 within which the abutment 26 is received so that the piston rod 23 is caused to move in unison with the slide 39. It should further be appreciated that the abutment 26 is captively located within the yoke 35 so as to move therewith. The trigger 14 is provided with a gear rack 40 which engages a gear pinion 41, which pinion 41 in turn engages a gear rack 42 formed from the slide 39. The pinion 41 would be fixed to and rotatably supported by the body 11. Accordingly depression of the trigger 14 causes movement of the slide 39 in the direction of the arrow 34. A spring 43 is also provided, and biases the slide 39 in the reverse direction to the arrow 34 in order to return the applicator 10 to the rest position. The spring 43, preferably, is a leaf spring located within handle 13 and trigger 14.

If so required, a heat supply member 36 could be provided and which projects into the interior of the piston rod 23 in order to heat the cream contained within the cartridge 15. The member 36 would extend to a heat source via the conduit 37. Preferably the conduit 37 would have a threaded member 38 enabling its fixing to the threaded portion 27 of the piston rod 23.

In operation of the abovedescribed applicator 10, a disposable cartridge is loaded into the applicator 10 and the trigger 14 depressed in order to cause movement of the piston rod 23 towards and into the chamber 18. This movement causes a predetermined volume of medicament to be delivered through the needle 29. Upon the piston rod 23 abutting the adjustment piston 30, the trigger 14 would be released and a spring would return the slide 39 to the rest postion. Accordingly the piston rod 23 would also be returned allowing communication between the chambers 18 and 20. Due to atmospheric pressure being applied to the sealed member 21, the sealed member 21 would move longitudinally into the chamber 20 forcing the chamber 18 to be reloaded with medicament from the reservoir chamber 20.

What we claim is:

1. A cartridge to receive a medicament to be dispensed, said cartridge having a longitudinal axis and comprising a delivery chamber, from which the medicament is dispensed, enclosed by a longitudinally extending side wall, a reservoir chamber enclosed by a further longitudinally extending side wall and having one end communicating with said delivery chamber and the other end closed by a sealed member movable longitudinally of said reservoir, a piston rod movable longitudinally through both chambers and sealingly engagable within said delivery chamber so that movement of said piston rod therealong delivers a predetermined volume of the medicament from within said delivery chamber, and the opposite movement of said piston rod exposes said delivery chamber to said reservoir chamber thereby enabling further medicament to be delivered from said reservoir chamber to said delivery chamber.

2. The cartridge of claim 1 wherein said delivery chamber and said reservoir chamber are both generally cylindrical in configuration, and said delivery chamber has a smaller diameter than said reservoir chamber.

3. The cartridge of claim 2 wherein said delivery chamber has a delivery end remote from said reservoir chamber, and said cartridge further includes a one-way valve assembly located in said delivery end and which restricts the medicament to move from said delivery chamber in a dispensing direction only.

4. The cartridge of claim 2 further including a piston surrounding said piston rod and being received within said reservoir chamber and movable therealong and closing one end of said reservoir chamber.

5. An applicator to receive a cartridge of medicament and to dispense predetermined volumes of the medicament from the cartridge, the cartridge consisting of:
   a reservoir chamber and a delivery chamber, with a piston rod extending through both chambers and having one extremity sealingly received within the delivery chamber;
   said applicator comprising:
   a body having socket means to receive said cartridge;
   a piston rod actuator, having means to engage said piston rod, said actuator being movably supported on said body so as to be movable from a first position locating the extremity of said piston rod in said reservoir chamber, and a second position locating said extremity in said delivery chamber, so as to cause a predetermined volume of said medicament to be delivered from said delivery chamber;
   trigger means mounted on said body and adapted to be manipulated by a user;
   said trigger being operatively associated with said actuator means to cause reciprocation thereof between the first and second positions.

6. The applicator of claim 1 wherein said actuator means is a slide to be mounted on said body, with said slide having yoke means which engages said piston rod.

7. The applicator of claim 6 including gear means operatively coupling said trigger means and said slide to cause reciprocation of said slide.

8. The applicator of claim 5 further including dose adjustment means to define the position of said cartridge within said body to thereby vary the stroke of said extremity within said delivery chamber, to thereby adjust the dose delivered by the applicator.

* * * * *